United States Patent [19]

Atkinson et al.

[11] 4,385,120

[45] May 24, 1983

[54] THERMOSTABLE GLYCEROKINASES AND PROCESS FOR ITS PRODUCTION

[75] Inventors: Anthony Atkinson, Salisbury, England; Michael J. Comer, Weilheim, Fed. Rep. of Germany

[73] Assignee: The Secretary of State for Defence in Her Britannic Majesty's Government of the United Kingdom of Great Britain and Northern Ireland, England

[21] Appl. No.: 284,115

[22] Filed: Jul. 16, 1981

Related U.S. Application Data

[63] Continuation-in-part of Ser. No. 824,606, Aug. 15, 1977, abandoned.

[30] Foreign Application Priority Data

Aug. 24, 1976 [GB] United Kingdom ............... 35258/76

[51] Int. Cl.$^3$ ....................... C12N 9/12; C12N 15/00; C12N 1/20; C12R 1/07
[52] U.S. Cl. .................................. 435/194; 435/172; 435/253; 435/832
[58] Field of Search ....................... 435/194, 253, 172

[56] References Cited

PUBLICATIONS

Chemical Abstracts, vol. 83, (1975), 129984s.
Lindgren et al., Journal of Bacteriology, Sep. 1976, vol. 127, No. 3, pp. 1047–1057.
Barman, Enzyme Handbook, vol. 1, (1969), pp. 401–402.
Atkinson et al., Journal Appl. Bacteriol., vol. 38, No. 3, pp. 301–304, (1975).

*Primary Examiner*—Lionel M. Shapiro
*Attorney, Agent, or Firm*—Stevens, Davis, Miller & Mosher

[57] ABSTRACT

A thermostable glycerokinase enzyme useful in the detection and estimation of glycerol derivatives has a half-life in excess of 1 hour at 55° C. at a protein concentration of less than 2 mg/ml and a pH of 7.8 ±0.5 in the absence of any substrate. The enzyme is produced by culturing at least one micro-organism which is capable of growth at a temperature of at least 50° C. in a culture medium in which it will produce said enzyme, disrupting the resulting cells of the micro-organism to release the enzyme and separating the enzyme from the cell debris. The medium normally contains at least 0.1% glycerol but certain strains of micro-organism have been found to be capable of producing thermostable glycerokinase enzyme even in the absence of glycerol. The micro-organism is preferably a Bacillus organism, especially of the *stearothermophilus* species.

24 Claims, No Drawings

THERMOSTABLE GLYCEROKINASES AND PROCESS FOR ITS PRODUCTION

This application is a continuation-in-part of application Ser. No. 824,606 filed Aug. 15, 1977, now abandoned.

The invention relates to new or improved glycerokinase enzymes and to processes for the production of such enzymes.

Glycerokinases are widely used in the detection and estimation of glycerol derivatives notably lipids in tissue and sera. However glycerokinases currently available are thermally unstable even at room temperature and require storage under refrigeration.

It has now been found that certain micro-organisms when grown in the presence of glycerol are capable of producing glycerokinase enzymes which are thermostable. The term "thermostable" as used herein refers to an enzyme having a half-life in excess of 1 hour at 55° C. at a protein concentration of less than 2 mg/ml and a pH of 7.8±0.5 in the absence of any substrate.

It has further been found that certain strains of micro-organisms are capable of producing thermostable glycerokinases even in the absence of glycerol.

According to one aspect of the present invention, therefore, there are provided glycerokinase enzymes which are thermostable (as defined above).

According to another aspect of the invention a process for the production of a thermostable glycerokinase comprises culturing at least one thermophilic micro-organism in a culture medium in which said micro-organism is capable of producing said enzyme, disrupting the resulting cells of the micro-organism to release the enzyme and separating the enzyme from the cell debris. (The term "thermophilic" as used herein denotes a micro-organism capable of growth at a temperature of at least 50° C.). Preferably the thermophilic micro-organism is of the genus Bacillus, for example naturally occuring or mutant strains of *B. coagulans, B. caldotenax, B. caldolyticus, B. caldovelox, B. subtilis* or *B. lichenoformis*. Especially suitable micro-organisms are those of the species *Bacillus stearothermophilus*, for example that formerly deposited with the National Canners Association under the number NCA 1503, now ATCC 7954 (also deposited as NCIB 8924).

The invention further provides mutant strains of the genus Bacillus which produce glycerokinase when cultured in the absence of glycerol or glycerol analogue. With these strains therefore thermostable glycerokinases may be produced by culturing the micro-organism in a medium which lacks glycerol or glycerol analogue. However in the case of both the micro-organisms which will and those which will not produce glycerokinases in the absence of glycerol or glycerol analogue, the culture medium will normally contain at least 0.1% by weight of glycerol or glycerol analogue though preferably less than 4.0% by weight. Most preferably the culture medium will contain 0.2% to 1.0% by weight of glycerol or glycerol analogue. The term glycerol analogue as used herein encompasses poly-functional $C_3$ alcohols, especially those containing two hydroxy groups, for example glyceric acid, L- or D-glyceraldehyde, dihydroxy acetone, or 3-mercapto-propan-1,3-diol.

The culture medium in either case may be a complex medium containing naturally-derived nutrient sources, such as peptones, yeast hydrolysates etc, or a defined salts medium containing inorganic and simple organic nutrient sources.

The culture is preferably conducted at a temperature of from 30° C. to 70° C., more especially from 50° to 65° C. (subject to the temperature tolerance of the micro-organism) and at a pH of from 5 to 8. It may be conducted under either aerobic or anaerobic conditions, though the former condition is preferred.

The cell disruption may be carried out by conventional techniques such as sonification, homogenisation or treatment with enzymes. Conventional enzyme isolation and purification techniques may then be used for example ion-exchange chromatography, fractionation on calcium phosphates, precipitation with ammonium sulphate or an organic solvent (eg. ethanol at 10 to 20% volume/volume concentration), gel filtration on dextrans, agarose or agarose-polyacrylamide and/or affinity chromatography on nucleotide derivatised matrices, or on sulphonic acid substituted monochlorotriazinyl ("Procion") dyes.

The thermostable glycerokinases produced from thermophilic microorganisms of the genus Bacillus typically have a structure composed of four identical or similar sub-units each of molecular weight 50,000 to 60,000. They bind to anion exchange resins and are stable at pH 5.0 in the presence of glycerol. They have a higher velocity constant (V max) at 60° C. than at 30° C.

Mutant strains of *Bacillus stearothermophilus* which produce glycerokinase when cultured in the absence of glycerol, i.e. constitutive mutants, may be obtained by environmental and selection pressure technique involving eg alternative growth in two media, one containing a substrate for the glycerokinase enzyme and the other free from such a substrate. Mutant strains of *B. stearothermophilus* can also be produced by irradiation with artificial UV having a wavelength of 254 mm. However none of the strains produced are usable for the production of glycerokinase in the absence of glycerol as the mutants have high reversion frequencies and revert too rapidly to their parent strains to be of practical value.

Examples of constitutive mutants produced by environmental and selection pressure techniques are the strains deposited with the National Collection of Industrial Bacteria under the numbers NCIB 11270 and NCIB 11271. These strains may be recognised as *B. stearothermophilus* by standard tests as described, for example, by Gordon, Haynes and Pang, Agricultural Handbook, U.S. Department of Agriculture (1973) Page 59. They may be recognised as constitutive mutants by the test of Ruch and Lin (J. Bacteriology Vol 124, 1975, No 1 page 348) as follows:

The strain is plated onto an agar plate containing a mixture of tryptic hydrolysate of casein and enzymatic digest of soya bean meal (Tryptone soya broth agar supplied by Oxid Ltd) and grown for 24 hours at 60° C. The plate is then sprayed with a solution of 10 g/l glycerol and 150 μg/ml chloramphenicol. The plate is incubated for a further hour at 60° C. and then sprayed with 10 g/l triphenyltetrazolium chloride in 1 Molar potassium phosphate, pH 7.5.

Colonies which are potentially constitutive are coloured pink to red.

Specific embodiments of the various aspects of the invention will now be described by way of example only. In these examples the media used were as follows:

| Complex medium | grm/liter |
|---|---|
| Tryptic meat digest (Bacto tryptone) | 20 |
| Yeast extract | 10 |
| $FeCl_3.6H_2O$ | 0.014 |
| $MnCl_2.4H_2O$ | 0.030 |
| $K_2SO_4$ | 2.6 |
| $MgSO_4.7H_2O$ | 0.54 |
| Citric Acid | 0.64 |
| $Na_2HPO_4.2H_2O$ | 6.4 |

"CA" medium

As described by Rowe, Goldberg and Amelunxen, J. Bateriology, Vol 124 (1975) No 1 p 279 except that all amino acids were omitted apart from methionine, valine and iso-leucine and the chromium chloride concentration was increased from 10 g/l to 30 g/l.

| Minimal medium (pH 7.2 ± 0.2) | grm/liter |
|---|---|
| $K_2HPO_4$ | 7 |
| Trisodium citrate | 0.5 |
| $MgSO_4.7H_2O$ | 0.1 |
| $(NH_4)_2SO_4$ | 1.0 |

The micro-organisms used were all of the genus Bacillus especially the species *Bacillus stearothermophilus* identified as described in the Gordon et al reference noted above at pages 212 (Table 21) and 214 (Table 22). Strain NCA 1503 is deposited as ATCC 7954 and is available to the public. The mutant strains mentioned are those deposited with public culture collections as listed in Table 1.

TABLE 1

| Designation herein | NCA 1503 | NCA 1503/3G | NCA 1503/47C |
|---|---|---|---|
| Deposit Nos NCIB | 8924 | 11270 | 11271 |
| ATCC | 7954 | | |

The mutant strains can be distinguished from NCA 1503 by the test for constitutive mutants described by Ruch and Lin (see above) in which both give deep red colourations, and by a number of biochemical properties. These are set out in Tables 2 to 6 below. The isolation of these mutants is described later.

TABLE 2

| | Sugar fermentation | | | | | |
|---|---|---|---|---|---|---|
| | NCA 1503 | | NCIB 11270 | | NCIB 11271 | |
| Sugar | Day 1 | Day 3 | Day 1 | Day 3 | Day 1 | Day 3 |
| Adonitol | − − | − − | − − | − − | − − | − − |
| Aesculin | − − | − − | − − | − − | − − | − − |
| Arabinose | − − | − − | − − | − − | − − | − − |
| Dextrin | − + | + + | − − | + + | − + | + + |
| Dextrose A/G | + + | + + | + + | + + | + + | + + |
| Dulcitol | − − | − − | − − | − − | − − | − − |
| Erythritol | − − | − − | − − | − − | w w | w w |
| Galactose | w w | w w | w − | − − | − − | − − |
| Glycerol | + + | + + | + + | + + | + + | + + |
| Glycogen | + + | + + | + + | + + | + + | + + |
| Inositol | − − | − − | w w | − − | w w | − − |
| Inulin | − − | − − | − − | − − | − − | − − |
| Lactose | − − | − − | w w | w w | w w | w w |
| Laevulose | − − | + + | w w | w w | − − | − − |
| Maltose | + + | + + | + + | + + | + + | + + |
| Mannose | + + | + + | + + | + + | + + | + + |
| Raffinose | − + | + + | − + | − + | + + | + + |
| Rhamnose | − − | − − | − − | − − | − − | − − |
| Saccharose | + + | + + | + + | + + | + + | + + |

TABLE 2-continued

| | Sugar fermentation | | | | | |
|---|---|---|---|---|---|---|
| | NCA 1503 | | NCIB 11270 | | NCIB 11271 | |
| Sugar | Day 1 | Day 3 | Day 1 | Day 3 | Day 1 | Day 3 |
| Salicin | − − | − − | − − | − − | − − | − − |
| Starch | + + | + + | + + | + + | + + | + + |
| Sorbitol | − − | − − | − − | − − | − − | − − |
| Trehalose | w w | + + | w w | + + | w w | + + |
| Xylose | − − | − − | − − | − − | − − | − − |
| Mannitol | − − | − − | w w | − − | w − | − − |

TABLE 3

| | Growth in: | | | | | |
|---|---|---|---|---|---|---|
| | NCA 1503 | | NCIB 11270 | | NCIB 11271 | |
| | Day 1 | Day 3 | Day 1 | Day 3 | Day 1 | Day 3 |
| Peptone + 1% NaCl | + + | + + | + + | + + | + + | + + |
| Peptone + 2% NaCl | + + | + + | + + | + + | + + | + + |
| Peptone + 3% NaCl | − − | + + | − − | − + | − − | − + |
| Peptone + 4% NaCl | − − | − − | − − | − − | − − | − − |
| Peptone + 5% NaCl | − − | − − | − − | − − | − − | − − |
| Citrate | − − | − − | − − | − − | − − | − − |

TABLE 4

| | Decomposition of: | | | | | |
|---|---|---|---|---|---|---|
| | NCA 1503 | | NCIB 11270 | | NCIB 11271 | |
| | Day 1 | Day 3 | Day 1 | Day 3 | Day 1 | Day 3 |
| Casein | − | − | − | + | − | + |
| Litmus milk | | | Clot; clear surface liquid | | | |
| Starch | w | + | − | + | w | + |

TABLE 5

| | Production of: | | |
|---|---|---|---|
| | NCA 1503 | NCIB 11270 | NCIB 11271 |
| Catalase | − | − | − |
| Oxidase | − | − | − |
| $NO_3$ Reductase | + | + | + |
| $NO_2$ Reductase | + | + | + |

TABLE 6

| | NCA 1503 | NCIB 11270 | NCIB 11271 |
|---|---|---|---|
| Growth at 37° C. | − | + | − |
| Growth at 70° C. | w | + | + |

In the following examples, enzyme activities are given in Units, defining 1 unit as 1μ mole of substrate (glycerol or glyceride) phosphorylated per minute at 30° C.

PRODUCTION OF GLYCEROKINASE FROM NON-CONSTITUTIVE BACILLUS ORGANISMS

Example 1

*B. stearothermophilus* NCA 1503 was grown in 100 ml of the complex medium (as described above) containing 4 g/l of glycerol in a 400 ml flask shaken at 200 rpm for 12–16 hours at 60° C. The resulting cell material was collected and assayed for glycerokinase activity. The yield of enzyme was 200 units/g dry cells.

The culture was repeated in the absence of glycerol when the yield of enzyme was less than 10 units/g dry cells.

Example 2

Example 1 was repeated using various strains of Bacillus. The yields of glycerokinase are shown in Table 7. The strains used were those isolated and identified by U. J. Heinen and W. Heinen, Arch. Microbiol. Vol 82, (1972), pages 1 to 23.

TABLE 7

| Species | YIELD (Units/g dry cells) |
| --- | --- |
| B. caldolyticus | 80 |
| B. caldotenax | 53 |
| B. caldovelox | 96 |

ISOLATION OF CONSTITUTIVE MUTANTS

A freeze dried sample of B. stearothermophilus NCA 1503 was reconstituted and grown in a shake flask at 60° C. in complex medium without glycerol. After 18 hrs a sample was transferred to a similar medium containing 4 g/l of glycerol. After a further 18 hrs a sample was transferred to an agar plate divided diagonally between minimal medium and complex medium with 20 g/l glycerol. The plate was incubated at 60° C. for 18 hrs and a colony smear from the left hand (defined salts medium) side of the plate was removed and suspended in physiological saline.

This culture was transferred to a second plate divided diagonally between minimal medium with 4 g/l glycerol and complex medium with 4 g/l glycerol. After culturing as above a single colony from the minimal medium region was removed and cultured through 3 cycles of complex medium without glycerol and followed by minimal medium with 4 g/l glycerol.

The resulting culture was plated onto Tryptone soya broth agar for the test of Ruch and Lin (see above) for constitutive mutants. The deepest red colony was selected and designated NCA 1503/3G (now NCIB 11270). After 3 passages through complex medium without glycerol the culture was replated onto Tryptone soya broth agar and the spray procedure repeated. A second mutant, NCA 1503/47C (now NCIB 11271) was selected as above.

PRODUCTION OF GLYCEROKINASE FROM CONSTITUTIVE MUTANTS

Examples 3-6

The mutants 3G and 47C isolated as described above were each grown in shake flasks as described in Example 1 both with and without glycerol. The enzyme yield in units per g dry cells are shown in Table 8.

TABLE 8

| Example | Strain Used | Glycerol CONC (g/l) | Yield Units/g Dry Cells |
| --- | --- | --- | --- |
| 3 | NCA 1503/3G | NIL | 250 |
| 4 | NCA 1503/3G | 4 | 1,230 |
| 5 | NCA 1503/47C | NIL | 310 |
| 6 | NCA 1503/47C | 4 | 1,870 |

Example 7

A 1 liter seed culture of B. stearothermophilus NCA 1503/3G was prepared at 60° C. in a stored complex medium containing 4 g/l of glycerol. This was used to seed a similar 20 liter seed culture.

A 400 liter culture vessel containing 400 liters of complex medium without glycerol at 60° C. was seeded with the 20 liter seed culture. Growth was continued at 60° C. and a controlled pH of 7.0±0.2 with aeration at 300 liters of air per minute and stirring at 250 rpm until the culture has an optical density of 0.8. 10 liters of 500 g/l glycerol was then added over one hour with the growth conditions unchanged. The culture was then continued under the same conditions until the carbon dioxide content of the effluent gas began to fall. The culture was then cooled to ambient temperature and the cells harvested in a De Laval centrifuge.

4.9 Kg of wet cell paste containing 1.1 million units of glycerokinase was obtained.

Example 8

Example 7 was repeated except that in place of the 10 liters of 500 g/l glycerol, 20 liters of a similar solution was added to the culture at a rate of 1 liter per hour.

9.0 Kg of wet cell paste containing 2.0±0.5 million units was obtained.

The cells were disrupted by homogenisation and the cell debris removed by centrifugation to yield a cell extract containing 1.04 units per mg of protein. The cell extract was then successively purified by pH precipitation at pH 5, chromatography on diethyl aminoethyl (DEAE) cellulose, ammonium sulphate precipitation, chromatography on DEAE cross-linked dextran (DEAE "Sephadex"), and by gel filtration on cross-linked dextran ("Sephadex" G200).

The resulting yields (based on the cell extract) and specific activities are given in Table 9.

TABLE 9

| Purification Step | Yield | Specific Activity (units/mg protein) |
| --- | --- | --- |
| Cell Extract | 100% | 1.04 |
| pH5 Supernatent | 80% | 3.5 |
| DEAE - cellulose eluate | 76% | 9.1 |
| Ammonium sulphate precipitate | 62% | 25 |
| DEAE - sephadex eluate | 55% | 60 |
| Gel filtration | 50% | 110 |

The purified enzyme was a tetramer composed of four identical or similar sub-units each of molecular weight 50,000-60,000. It had half-life at pH 7.5 in the presence of substrate at 60° C., of greater than 3 hours falling to approximately 35 minutes at 65° C., 18 mins at 70° C. and 3 minutes at 80° C. It had half-lives in the presence of glycerol at +4° C. of greater than 24 hours at pH 3.5, 48 hours at pH 4.9 and 2 months at pH 6.0 or 7.5.

The velocity constants ($V_{max}$) at various temperatures relative to that at 30° C. are shown in Table 10.

TABLE 10

| Temp °C. | $V_{max}$ |
| --- | --- |
| 20 | 67 |
| 25 | 71 |
| 30 | 100 |
| 37 | 125 |
| 45 | 144 |
| 60 | 260 |

What is claimed is:

1. A process for producing a substantially pure thermostable glycerokinase enzyme wherein the enzyme has a half life in excess of 1 hour at a protein concentration of less than 2 mg/ml and a pH of 7.5±0.5 in the absence of any substrate which comprises culturing, in batch culture, at least one micro-organism of the genus Bacillus that is capable of growth at a temperature of at least 50° C., in a culture medium in which said at least one micro-organism is capable of producing said glycerokinase enzyme, disrupting the resulting cells of said at least one micro-organism to release said enzyme, and separating said enzyme from the cell debris.

2. A process according to claim 1, wherein the culture medium contains at least 0.1% by weight of glycerol or glycerol analogue.

3. A process according to claim 2, wherein the culture medium contains less than 4.0% by weight of glycerol or glycerol analogue.

4. A process according to claim 2, wherein the culture medium contains from 0.2 to 1.0% by weight of glycerol or glycerol analogue.

5. A process according to claim 1 wherein the micro-organism is of the species *Bacillus stearothermophilus*.

6. A process according to claim 1, wherein the culture medium comprises a complex medium containing naturally-derived nutrient sources.

7. A process according to claim 1, wherein the culture is conducted at a temperature of from 30° C. to 70° C. and at a pH of from 5 to 8.

8. A process according to claim 1, wherein the culture is conducted at a temperature of from 50° to 65° C.

9. A process according to claim 1 wherein the culture is conducted under aerobic conditions.

10. A process according to claim 1, wherein the cells are disrupted by a method selected from the group consisting of sonification, homogenisation and enzyme treatment.

11. A process according to claim 1, wherein the enzyme is separated from the cell debris by subjecting said debris to at least one treatment selected from the group consisting of ion-exchange chromatography fractionation on calcium phosphates, precipitation with ammonium sulphate, precipitation with an organic solvent, gel filtration on a material selected from the group consisting of dextrans, agarose and agarose-polyacrylamide, affinity chromatography on nucleotide derivatised matrices and affinity chromatography on sulphonic acid substituted monochlorotriazinyl dyes.

12. A process according to claim 11, wherein the enzyme is separated from the cell debris by a process including precipitation with ethanol at a concentration of from 10 to 20% volume/volume.

13. A process for producing a glycerokinase enzyme preparation having a half-life in excess of 1 hour at 55° C. at a protein concentration of less than 2 mg/ml and a pH of 7.5±0.5 in the absence of any substrate, said process comprising culturing the micro-organism of the species *Bacillus stearothermophilus* deposited as NCIB 11270 in a culture medium in which said micro-organism is capable of producing said glycerokinase enzyme, disrupting the resulting cells of the said micro-organism to release the enzyme and separating the enzyme from the resulting cell debris.

14. A process for producing a glycerokinase enzyme preparation having a half-life in excess of 1 hour at 55° C. at a protein concentration of less than 2 mg/ml and a pH of 7.5±0.5 in the absence of any substrate, said process comprising culturing the micro-organism of the species *Bacillus stearothermophilus* deposited as NCIB 11271 in a culture medium in which said micro-organism is capable of producing said glycerokinase enzyme, disrupting the resulting cells of the said micro-organism to release the enzyme and separating the enzyme from the resulting cell debris.

15. A process for producing a strain of a micro-organism which is capable of producing a glycerokinase enzyme when cultured in the absence of glycerol which comprises subjecting at least one micro-organism of the species *Bacillus stearothermophilus* to environmental pressure selection by alternate growth in two media, one containing a substrate for said glycerokinase enzyme and the other free from such a substrate.

16. A substantially pure thermostable glycerokinase enzyme wherein the enzyme has a half life in excess of 1 hour at 55° C. at a protein concentration of less than 2 mg/ml and a pH of 7.5±0.5 in the absence of any substrate obtained in accordance with the process of claim 1.

17. The glycerokinase enzyme of claim 16 derived from a biologically pure culture of a mutant strain of *Bacillus stearothermophilus* that is capable of growth at a temperature of at least 50° C. and that is capable of producing said glycerokinase enzyme when cultured in the absence of glycerol.

18. The glycerokinase enzyme of claim 17 derived from a micro-organism selected from the group consisting of *Bacillus stearothermophilus* NCIB 11270 and NCIB 11271.

19. A process for producing the glycerokinase of claim 17, said process comprising culturing, in batch culture, a biologically pure culture of a mutant strain of *Bacillus stearothermophilus* that is capable of producing said glycerokinase enzyme when cultured in the absence of glycerol, in a culture medium in which said micro-organism is capable of producing said glycerokinase enzyme, disrupting the resulting cells of said micro-organism to release said enzyme, and separating said enzyme from the resulting debris.

20. A process for producing the glycerokinase enzyme of claim 18, said process comprising culturing in batch culture, the micro-organism of the species *Bacillus stearothermophilus* deposited as NCIB 11270 in a culture medium in which said micro-organism is capable of producing said glycerokinase enzyme, disrupting the resulting cells of said micro-organism to release said enzyme, and separating said enzyme from the resulting cell debris.

21. A process for producing the glycerokinase enzyme of claim 18, said process comprising culturing, in batch culture, the micro-organism of the species *Bacillus stearothermophilus* deposited as NCIB 11271 in a culture medium in which said micro-organism is capable of producing said glycerokinase enzyme, disrupting the resulting cells of said micro-organism to release the enzyme, and separating the enzyme from the resulting cell debris.

22. A biologically pure culture of a mutant strain of *Bacillus stearothermophilus* that is capable of growth at a temperature of at least 50° C. and that is capable of producing the glycerokinase enzyme of claim 17 when cultured in the absence of glycerol.

23. A biologically pure culture of a mutant strain of *Bacillus stearothermophilus* that produces glycerokinase when cultured in the absence of glycerol wherein said mutant strain is the micro-organism deposited as NCIB 11270.

24. A biologically pure culture of a mutant strain of *Bacillus stearothermophilus* that produces glycerokinase when cultured in the absence of glycerol wherein said mutant strain is the micro-organism deposited as NCIB 11271.

* * * * *